United States Patent [19]

Tomcufcik et al.

[11] Patent Number: 4,914,234

[45] Date of Patent: * Apr. 3, 1990

[54] 10,10-DIHYDRO-10-((SUBSTITUTED-CARBONYL)IMINO)-10-PHENYL-10H-PHENOXAPHOSPHINE, HYDROCHLORIDE

[75] Inventors: Andrew S. Tomcufcik, Bergen, N.J.; Joseph W. Marsico, Rockland, N.Y.; Nancy H. Eudy, Orange, N.Y.; Howard Newman, Rockland County, N.Y.

[73] Assignee: American Cyanamid Company, Stamford, Conn.

[*] Notice: The portion of the term of this patent subsequent to Oct. 11, 2005 has been disclaimed.

[21] Appl. No.: 228,894

[22] Filed: Aug. 4, 1988

Related U.S. Application Data

[62] Division of Ser. No. 61,981, Jul. 27, 1987, Pat. No. 4,777,290, which is a division of Ser. No. 836,278, Mar. 5, 1986, Pat. No. 4,689,324.

[51] Int. Cl.$^4$ .............................................. C07F 9/02
[52] U.S. Cl. ...................................................... 564/12
[58] Field of Search ........................................... 564/12

[56] References Cited

U.S. PATENT DOCUMENTS 4,689,324 8/1987 Tomcufcik et al. .................. 564/12
4,777,290 10/1988 Tomcufcik et al. .................. 564/12

Primary Examiner—Anton H. Sutto

Attorney, Agent, or Firm—H. G. Jackson

[57] ABSTRACT

Novel 10,10-Dihydro-10-[substituted carbonyl)imino]-10-phenyl-10H-phenoxaphines of the formula:

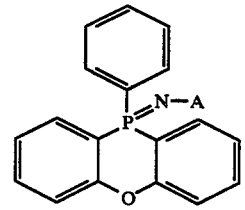

wherein A is selected from the group consisting of hydrogen and $COOR_1$, where, when A is hydrogen the compound is in the form of a water soluble salt $H_nX$, where n is an integer 1 or 2 and X is selected from the group consisting of sulfate, trefluoroacetate, bromide and chloride and $R_1$ is selected from the group consisting of straight or branched chain alkyl($C_1$-$C_4$), alkenyl($C_2$-$C_4$), alkynyl($C_2$-$C_4$), cycloalkyl($C_3$-$C_6$), cycloalkyl($C_3$-$C_6$)methyl, benzyl, pyridylmethyl and tetrahydro-3-furanyl; methods for using these compounds for effecting diuresis, treating hypertension and edema and lowering plasma renin activity in mammals; pharmaceutical compositions of matter containing these compounds and processes for their preparation.

1 Claim, No Drawings

10,10-DIHYDRO-10-((SUBSTITUTED-CARBONYL-)IMINO)-10-PHENYL-10H-PHENOXAPHOS-PHINE, HYDROCHLORIDE

This is a division of application, Ser. No. 061,981, filed July 27, 1977, now 4,777,290 which is a division of application Ser. No. 836,278 filed Mar. 5, 1986, now U.S. Pat. No. 4,689,324 issued Aug. 25, 1987.

SUMMARY OF THE INVENTION

This invention is concerned with new compounds of the formula:

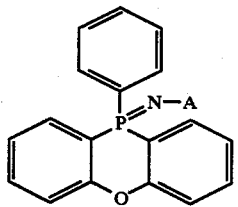

FORMULA I wherein A is selected from the group consisting of hydrogen and $COOR_1$, where, when A is hydrogen the compound is in the form of a water soluble salt HnX, where n is an integer 1 or 2 and X is selected from the group consisting of sulfate, trifluoroacetate, bromide and chloride and $R_1$ is selected fromm the group consisting of straight or branched chain alkyl($C_1$-$C_4$), alkenyl($C_2$-$C_4$), alkynyl($C_2$-$C_4$), cycloalkyl($C_3$-$C_6$), cycloalkyl($C_3$-$C_6$)methyl, benzyl, pyridylmethyl and tetrahydro-3-furanyl.

This invention is also concerned with methods of using these compounds to effect diuresis, treat hypertension and edema, and lower plasma renin activity in mammals, as well as pharmaceutical compositions of matter containing these compounds and processes for the preparation of these compounds.

DETAILED DESCRIPTION OF THE INVENTION

In accordance with the present invention, there are provided methods of effecting diuresis and lowering plasma renin activity in a mammal which comprises administering to said mammal a therapeutically effective amount of a compound selected from those of Formula I.

The compounds of Formula I find utility as diuretics and cardiotonics in mammals and as such may be used as the drug of choice for the treatment of edema caused by cardiac, hepatic, pulmonary and renal diseases, as well as drug-induced fluid and salt retention. These compounds may also be useful as hypotensive agents upon chronic administration by virture of their diuretic activity. As cardiotonic agents, these compounds may likewise be useful in the treatment of congestive heart failure.

The action of the currently available diuretics can be depicted by the following diagram:

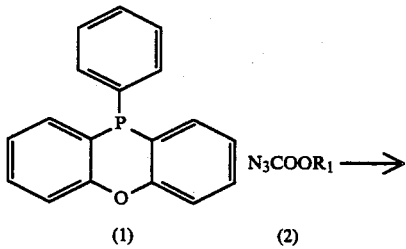

In contrast, the compounds of the present invention acting on the kidney lower plasma renin activity, thereby effecting non-attenuated sodium loss and minimal potassium loss, and preventing adrenal compensation.

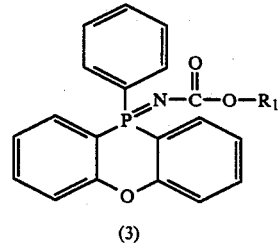

The compounds of this invention may be prepared as described in the following flowcharts and text.

FLOWCHART A

In accordance with Flowchart A, 10-phenyl-10H-phenoxaphosphine (1), which is a known compound [J. Granoth, et al., J. Chem. Soc., Perkin II, pp. 697–700 (1972)], is reacted with a carbonazidate (2), where $R_1$ is alkyl($C_1$-$C_4$) or phenylmethyl in ether, giving the products (3). The requisite $N_3COOR_1$ are obtained by treating carbazidic esters of the structure $H_2NNHCOOR_1$ with nitrous acid, or by the action of chloroformic esters of the structure $ClCOOR_1$, with lithium or sodium azide.

FLOWCHART B

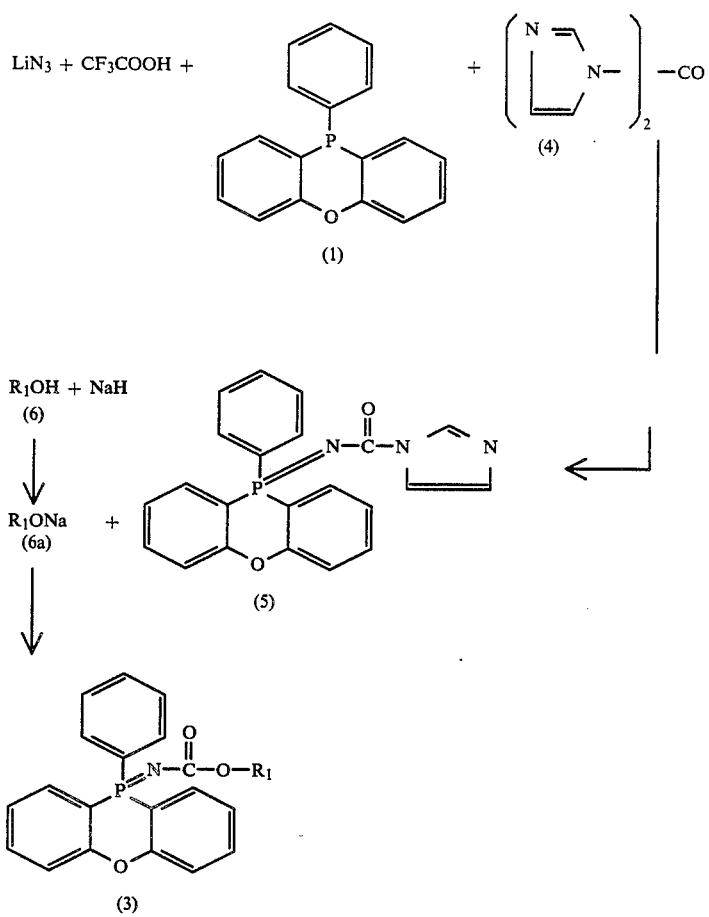

In accordance with Flowchart B, lithium azide and trifluoroacetic acid are reacted in acetonitrile at $-10°$ to $+10°$ C. for 1-2 hours, then with a solution of 10-phenyl-10H-phenoxyaphosphine (1) and N,N-carbonyldiimidazole in acetonitrile at room temperature for 4–8 hours, giving 10,10-dihydro-10-[(1H-imidazol-1-ylcarbonyl)-imino]-10-phenyl-10H-phenoxaphosphine (5) which is then reacted with a sodium alkoxide (6a) prepared from an alcohol (6) and sodium hydride where $R_1$ is selected from the group comprising alkenyl($C_2$–$C_4$), alkynyl($C_2$–$C_4$), cycloalkyl($C_3$–$C_6$), cycloalkyl($C_3$–$C_6$)methyl, pyridylmethyl and 3-hydroxytetrahydrofuran in 1,2-dimethoxyethane, giving the products (3).

Flowchart C

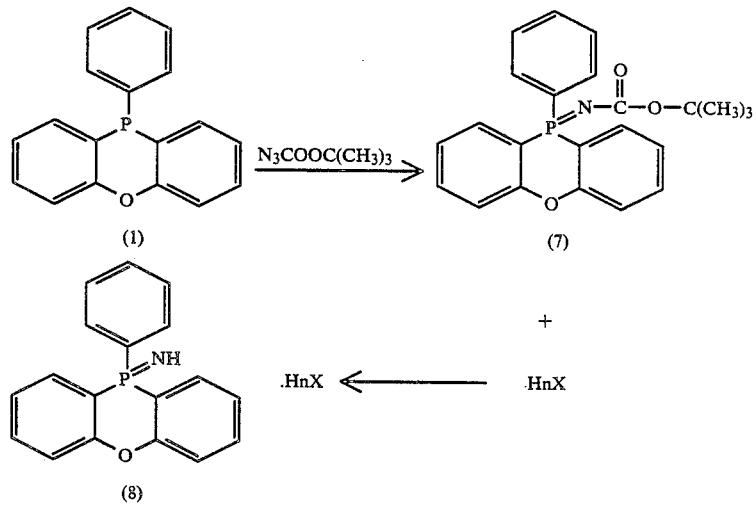

In accordance with Flowchart C. 10-phenyl-10H-phenoxaphosphine (1) is reacted with t-butyl carbonazidate in ether, giving 10-[[(1,1-dimethylethoxy)carbonyl]-imino]-10,10-dihydro-10-phenyl-10H-phenoxaphosphine (7) which is then reacted with an appropriate acid HnX and isolated from ether, giving compounds (8) where n and X are as described above.

Flowchart D

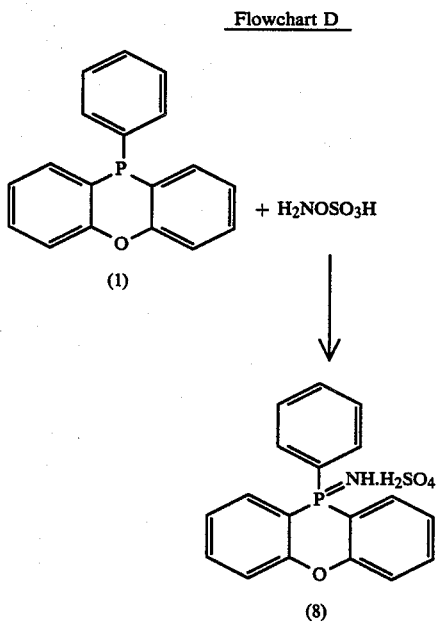

In accordance with Flowchart D. 10-phenyl-10H-phenoxaphosphine (1) is reacted with hydroxylamine 0-sulfonic acid in anhydrous methanol for several hours, then added to ether giving 10,10-dihydro-10-imino-10-phenyl-10H-phenoxaphosphine sulfate.

Flowchart E

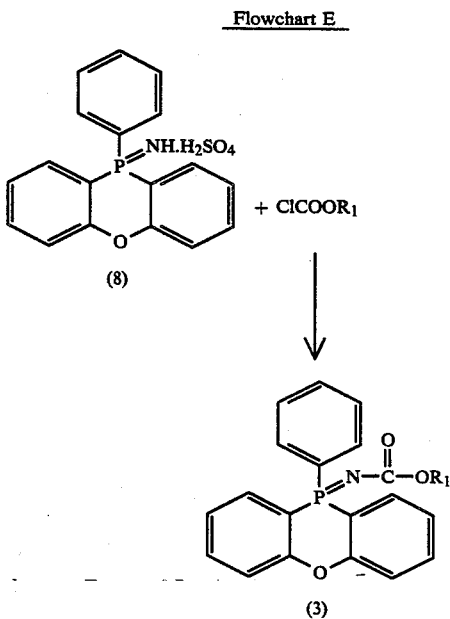

In accordance with Flowchart E, 10,10-dihydro-10-imino-10-phenyl-10H-phenoxaphosphine sulfate (8) and triethylamine in acetonitrile are reacted with a chloroformate ClCOOR$_1$, where R$_1$ is as described above, for several hours, giving (3).

Inhibition of evoked increase of plasma renin activity was determined by the following test.

Compounds were tested for their ability to prevent drug-induced elevation of plasma renin activity (PRA) in concious, male Wistar rats (180–200 g, Charles River Lab.). PRA elevation was induced by a combined oral provocative treatment (C) of hydrochlorothiazide (10 mg/kg) and 1-(3-benzoyl-3-mercapto-2-methylpropionyl-L-proline, acetate (U.S. Pat. No. 4,226,775) (1 mg/kg), prepared by compounding in a mortar and pestle with preboiled 3% starch suspension. This treatment provided the daily maximum PRA. The daily minimum PRA was obtained from rats given oral starch suspension (S) alone. The magnitude of drug effect on PRA elevation was ascertained from rats pretreated orally with test agent (D), at the indicated doses, 30 minutes prior to administration of provocative treatment (C). The test agent was also compounded in preboiled 3% starch suspension. The dose volumes for both pretreatment and provocative treatment were 2 ml/kg. One hour after provocative treatment the rats were sacrificed by decaption and the first 3 seconds of blood collected in two chilled vacutainer tubes containing 40 µl of 150 mg/ml tripotassium EDTA. The plasmas, which were obtained by centrifugation for 20 minutes at 4° C. and 3000×G, were incubated (one of each pair at 37° C., the other at 4° C.) at pH 6.8 in 50 mM phosphate buffer to produce angiotensin I. The incubates contained peptidase inhibitors to prevent angiotensin I degradation and the incubation buffer contained 1 mg/ml lysozyme (Sigma Grade III) used as an antiabsorbant. The incubates were diluted 20 fold in cold 100 mM tris buffer (pH adjusted to 7.4 with glacial acetic acid) also containing 1 mg/ml lysozyme, and then frozen. Diluted incubates were assayed within 3 days for angiotensin I content by radioimmunoassay according to a modification of the method of Haber, et al., J. Clin. Endocrin., 29, 1349–1355 (1969).

PRA is calculated as follows: PRA(mg AI/hour/ml plasma)=PRA 37° C.-PRA 4° C. Percent inhibition of PRA elevation is calculated as follows:

$$\% \text{ Inhibition} = 100 \times \frac{[PRA(C) - PRA(D)]}{[PRA(C) - PRA(S)]}$$

The results of this test on a representative compound of this invention appear in Table I.

TABLE I

| Percent Inhibition of Plasma Renin Elevation | | |
|---|---|---|
| Compound | Dose (mg/kg) | Av. % Inhibition (No. of Rats) |
| 10-[(Ethoxycarbonyl)imino]-10,10-dihydro-10-phenyl-10H-phenoxaphosphine | 1 | 33(5) |
| | 2 | 54(5) |
| | 4 | 78(5) |
| | 8 | 91(5) |
| | 25 | 84(5) |
| 10,10-Dihydro-10-imino-10-phenyl-10H-phenoxaphosphine, sulfate | 1 | 38(7) |
| | 2 | 31(13) |
| | 4 | 42(13) |
| | 8 | 67(10) |

The diuretic activity of the compounds of this invention was determined according to the method of Chan, P. S. and Poorvin, D., Sequential method for combined screening antihypertensive and diuretic agents in the same spontaneously hypertensive rat. Clinical and Experimental Hypertension, 1 (6), 817–830 (1979).

Male spontaneously hypertensive rats of Okamoto strain, 16 weeks old, Taconic Farms Inc., were used in the test. These rats were kept on Purina laboratory chow and tap water ad libitum for 8 weeks before use. The male adult rats (about 300 g) were dosed by gavage with a test compound at 100 mg/kg at zero hour with the exception of one male adult rat in which the test compound dosage was 50 mg/kg. The test compound was suspended in 3% preboiled starch at 50 mg/ml. Each rat was put in metabolism cage. The 0–5 hour urine was collected and urinary sodium and potassium were determined using a Beckman Astra 4. The results of this test on representative compounds of this invention appear in Table II.

TABLE II

Diuretic Activity in Spontaneously Hypertensive Rats

| Compound | Volume ml | Sodium MEQ/ 5 Hours | Potassium MEQ/ 5 Hours |
| --- | --- | --- | --- |
| 10,10-Dihydro-10-[(ethoxycarbonyl)imino]-10-phenyl-10H-phenoxaphosphine | 19.0 | 2.20 | 0.49 |
| 10,10-Dihydro-10-[(methoxycarbonyl)imino]-10-phenyl-10H-phenoxaphosphine | 14.0 | 1.48 | 0.74 |
| 10,10-Dihydro-10-[[(1-methylethoxy)carbonyl]imino]-10-phenyl-10H-phenoxaphosphine | 16.5 | 2.30 | 0.66 |
| 10,10-Dihydro-10-[[(2-methylpropoxy)carbonyl]imino]-10-phenyl-10H-phenoxaphosphine | 12.8 | 1.63 | 0.64 |
| 10,10-Dihydro-10-phenyl-10-[[(phenylmethoxy)carbonyl]imino]-10H-phenoxaphosphine | 12.3 | 1.32 | 0.56 |
| 10-[[(Cyclopropylmethoxy)carbonyl]imino]-10,10-dihydro-10-phenyl-10H-phenoxaphosphine | 10.8 | 1.41 | 0.75 |
| 10,10-Dihydro-10-phenyl-10-[[[(tetrahydro-3-furanyl)oxy]carbonyl]imino]-10H-phenoxaphosphine | 14.3 | 1.49 | 0.73 |
| 10,10-Dihydro-10-phenyl-10-[[(2-propenyloxy)carbonyl]imino]-10H-phenoxaphosphine | 12.0 | 1.27 | 0.61 |
| 10,10-Dihydro-10-phenyl-10-[[(2-propynyloxy)carbonyl]imino]-10H-phenoxaphosphine | 10.5 | 1.13 | 0.61 |
| 10-[[(Cyclopentyloxy)carbonyl]imino]-10,10-dihydro-10-phenyl-10H-phenoxaphosphine | 14.0 | 1.71 | 0.60 |
| 10,10-Dihydro-10-phenyl-10-[[(3-pyridylmethoxy)carbonyl]imino]-10H-phenoxaphosphine | 20.5 | 2.61 | 0.59 |
| 10,10-Dihydro-10-phenyl-10-[[(4-pyridylmethoxy)carbonyl]imino]-10H-phenoxaphosphine | 18.0 | 2.28 | 0.40 |
| 10,10-Dihydro-10-phenyl-10-[[(2-pyridylmethoxy)carbonyl]imino]-10H-phenoxaphosphine* | 10.8* | 1.26* | 0.74* |
| 10,10-Dihydro-10-imino-10-phenyl-10H-phenoxaphosphine, sulfate | 9.8 | 1.56 | 0.18 |
| 10,10-Dihydro-10-imino-10-phenyl-10H-phenoxaphosphine, bis(trifluoroacetate) | 12.5 | 1.16 | 0.66 |
| 10,10-Dihydro-10-phenyl-10H-phenoxaphosphine, hydrobromide | 8.0 | 1.12 | 0.26 |
| 10,10-Dihydro-10-imino-10-phenyl-10H-phenoxaphosphine, hydrochloride | 16.5 | 2.01 | 0.59 |

*Dosage = 50 mg/kg

The compounds of the present invention have been found to be highly useful for lowering plasma renin activity and as diuretics in mammals when administered in amounts ranging from about 1.0 mg to about 30 mg/kg of body weight per day. A preferred dosage regimen for optimum results would be from about 3.0 mg to about 20.0 mg/kg of body weight per day. Such dosage units are employed that a total of from about 200 mg to about 1400 mg of active compound for a subject of about 70 kg of body weight are administered in a 24 hour period. This dosage regimen may be adjusted to provide the optimum therapeutic response. For example, several divided doses may be administered daily or the dose may be proportionally reduced as indicated by the exigencies of the therapeutic situation. The compounds of this invention are preferably administered orally but may be administered in any convenient manner such as by the intravenous, intramuscular, or subcutaneous routes, in appropriate quantities.

The active compounds of the present invention may be orally administered, for example, with an inert diluent or with an assimilable edible carrier, or they may be enclosed in hard or soft shell gelatin capsules, or they may be compressed into tablets, or they may be incorporated directly with the food of the diet. For oral therapeutic administration, the active compounds may be incorporated with excipients and used in the form of tablets, troches, capsules, elixirs, suspensions, syrups, wafers and the like. Such compositions and preparations should contain at least 0.1% of active compound. The percentage of the compositions and preparations may, of course, be varied and may conveniently be between about 2% to about 60% of the weight of the unit. The amount of active compound in such therapeutically useful compositions is such that a suitable dosage will be obtained.

The tablets, troches, pills, capsules and the like may also contain the following: A binder such as gum tragacanth, acacia, corn starch or gelatin; excipients such as dicalcium phosphate; a disintegrating agent such as corn starch, potato starch, alginic acid and the like; a lubricant such as magnesium stearate; and a sweetening agent such as sucrose, lactose or saccharin may be added or a flavoring agent such as peppermint, oil of wintergreen or cherry flavoring. When the dosage unit form is a capsule, it may contain, in addition to materials of the above type, a liquid carrier such as a fatty oil. Various other materials may be present as coatings or to otherwise modify the physical form of the dosage unit. For instance, tablets, pills or capsules may be coated with shellac, sugar or both. A syrup or elixir may contain the active compound, sucrose as a sweetening agent, methyl and propylparabens as preservatives, a dye and flavoring such as cherry or orange flavor. Of course, any material used in preparing these dosage unit forms must be pharmaceutically pure and nontoxic.

The sulfate salt of 10,10-dihydro-10-imino-10-phenyl-10H-phenoxaphosphine, being stable in solution, may be adminstered parenterally. Solutions of the sulfate salt can be prepared in water suitably mixed with a surfactant such as hydroxypropylcellulose. Dispersions can also be prepared in glycerol, liquid polyethylene glyocos and mixtures thereof and in oils. Under ordinary conditions of storage and use, these preparations contain a preservative to prevent the growth of microorganisms.

The pharmaceutical forms suitable for injectable use include sterile aqueous solutions or dispersions and sterile powders for the extemporaneous preparation of sterile injectable solutions or dispersions. In all cases the form must be sterile and must be fluid to the extent that easy syringability exists. It must be stable under the conditions under the conditions of manufacture and storage and must be preserved against the contaminating action of microorganisms such as bacteria and fungi. The carrier can be a solvent or dispersion medium containing for example, water, ethanol, polyol (for example, glycerol, propylene glycol, and liquid polyethylene glycol, and the like), suitable mixtures thereof, and vegetable oils. The proper fluidity can be maintained, for example, by the use of a coating such as lecithin, by the maintenance of the required particle size in the case of dispersions and by the use of surfactants. The prevention of the action of microorganisms can be brought about by various antibacterial and antifungal agents, for example, parabens, chlorobutanol, phenol, sorbic acid, thimersal, and the like. In many cases, it will be preferable to include isotonic agents, for example, sugars or sodium chloride. Prolonged absorption of the injectable compositions can be brought about by the use in the compositions of agents delaying absorption, for example, aluminum monostearate and gelatin.

Sterile injectable solutions are prepared by incorporating the active compound in the required amount in the appropriate solvent with various of the other ingredients enumerated above, as required, followed by filtered sterilization. Generally, dispersions are prepared by incorporating the various sterilized active ingredients into a sterile vehicle which contains the basic dispersion medium and the other required ingredients from those enumerated above. In the case of sterile powders for the preparation of sterile injectable solutions, the preferred methods of preparation are vacuum drying and the freeze-drying techniques which yield a powder of the active ingredient plus any additional desired ingredient from a previously sterile-filtered solution thereof.

As used herein, "pharmaceutically acceptable carrier" includes any and all solvents, dispersion media, coatings, antibacterial and antifungal agents, isotonic and absorption delaying agents and the like. The use of such media and agents for pharmaceutically active substances is well known in the art. Except insofar as any conventional medium or agent is incompatible with the active ingredient, its use in the therapeutic compositions is contemplated.

It is especially advantageous to formulate parenteral compositions in dosage unit form for ease of administration and uniformity of dosage. Dosage unit form, as used herein, refers to physically discrete units suited as unitary dosages for the mammalian subjects to be treated each unit containing a predetermined quantity of active material calculated to produce the desired therapeutic effect in association with the required pharmaceutical carrier. The specification for the novel dosage unit forms of the invention are dictated by, and directly dependent on, the unique characteristics of the active material and the particular therapeutic effect to be achieved, and the limitations inherent in the art of compounding such an active material for the treatment of disease in living subjects having a diseased condition in which bodily health is impaired as herein disclosed in detail.

The invention will be described in greater detail in conjunction with the following non-limiting examples.

EXAMPLE 1

10,10-Dihydro-10-[(ethoxycarbonyl)imino]-10-phenyl-10H-phenoxaphosphine

The compound 10-phenyl-10H-phenoxaphosphine was prepared by the method of J. Granoth, et al., J. Chem. Soc., Perkin II, pp. 697-700 (1972).

A solution of 1.50 g of 10-phenyl-10H-phenoxaphosphine in ether was filtered through diatomaceous earth. To the filtrate was added dropwise a solution of 0.95 g of ethyl carbonazidate in 5.7 ml of ether. This mixture was stirred overnight, when the crystals were collected, washed with ether and dried in vacuo for 3 hours at 50° C., giving 970 mg of the desired product, mp 160°–162° C. (dec.).

EXAMPLE 2

10,10-Dihydro-10-[(methoxycarbonyl)imino]-10-phenyl-10H-phenoxaphosphine

To a solution of 1.46 g of 10-phenyl-10H-phenoxaphosphine in 20 ml of ether was added with stirring, a solution of 0.8 g of methyl carbonazidate in 7 ml of ether. This mixture was stirred for 2 hours, then allowed to stand and the crystals were collected, washed with ether and dried overnight at 40° C., giving 1.26 g of the desired product, mp 181°–184° C. (dec.).

EXAMPLE 3

10,10-Dihydro-10-[[(1-methylethoxy)carbonyl]imino]-10-phenyl-10H-phenoxaphosphine A 1.5 g portion of isopropyl chloroformate was dissolved in 25 ml of acetonitrile. This solution was stirred at 0.5° C. as 1.0 g of lithium azide was added. This mixture was stirred for 16 hours, then 50 ml of ether was added and the mixture filtered into a solution of 2.5 g of 10-phenyl-10H-phenoxaphosphine in 50 ml of ether. This mixture was stirred for 30 minutes, then allowed to stand for 3 hours. The solid was collected, washed with ether and dried in vacuo at 60° C., giving 0.3 g of the desired product, mp 191°–192° C.

EXAMPLE 4

10,10-Dihydro-10-[[(2-methylpropoxy)carbonyl]imino]-10-phenyl-10H-phenoxaphosphine The procedure of Example 3 was repeated using 1.6 g of isobutyl chloroformate in place of the isopropyl chloroformate. The final reaction mixture was evaporated in vacuo to a viscous oil. This oil was stirred with 100 ml of ether, then the crystals were collected, washed with ether and dried in vacuo at 60° C., giving 2.1 g of the desired product, mp 142°–143° C.

EXAMPLE 5

10,10-Dihydro-10-phenyl-10-[[(phenylmethoxy)-carbonyl]imino]-10H-phenoxaphosphine The procedure of Example 4 was repeated using 2.1 g of benzyl chloroformate in place of the isobutyl chloroformate, giving 1.7 g of the desired product, mp 148°–150° C.

EXAMPLE 6

10,10-Dihydro-10-[(1H-imidazol-1-ylcarbonyl)imino]-10-phenyl-10H-phenoxaphosphine To a mixture of 6.0 g of trifluoroacetic acid in 100 ml of acetonitrile at 0° C. was added 5.0 g of lithium azide. This mixture was stirred at 0°–5° C. for 90 minutes, then a solution of 11.0 g of 10-phenyl-10H-phenoxaphosphine and 7.0 g of N,N-carbonyldiimidazole in 200 ml of acetonitrile was added. This mixture was stirred at room temperature for 5 hours, then diluted with 500 ml of water. The solid was collected, washed with water and dried in vacuo at 60° C., giving 13.5 g of 10,10-dihydro-10-[(1H-imidazol-1-ylcarbonyl)imino]-10-phenyl-10H-phenoxaphosphine, mp 225°–226° C.

EXAMPLE 7

10-[[(Cyclopropylmethoxy)carbonyl]imino]-10,10-dihydro-10-phenyl-10H-phenoxaphosphine A 1.0 g portion of cyclopropylmethanol was dissolved in 100 ml of 1,2-dimethoxyethane. This solution was treated with 0.6 g of 50% sodium hydride in oil and stirred for 30 minutes. A 3.8 g portion of 10,10-dihydro-10-[(1H-imidazol-1-ylcarbonyl)imino]-10-phenyl-10H-phenoxaphosphine was added and this mixture was stirred at reflux for 16 hours, then cooled, diluted with 200 ml of water and stored at −10° C. This suspension was extracted with 500 ml of dichloromethane. The dichloromethane layer was dried over magnesium sulfate, filtered and the filtrate evaporated to a viscous oil. This oil was stirred with 100 ml of ether overnight, then the precipitate was collected, washed with ether and dried in vacuo at 60° C., giving 0.3 g of the desired product, mp 163°–166° C.

EXAMPLE 8

10,10-Dihydro-10-phenyl-10-[[[(tetrahydro-3-furanyl)-oxy]carbonyl]imino]-10H-phenoxaphosphine A mixture of 0.85 ml of 3-hydroxytetrahydrofuran, 50 ml of 1,2-dimethoxyethane and 0.5 g of 50% sodium hydride in oil was stirred for ½ hour. A 3.8 g portion of 10,10-dihydro-10-[(1H-imidazol-1-ylcarbonyl)imino]-10-phenyl-10H-phenoxaphosphine was added, the mixture was refluxed for 6 hours and then concentrated to a thick gum. Water was added and the resulting solid collected and recrystallized from dichloromethane-hexane with charcoal treatment and refrigeration, giving 2.50 g of the desired product, mp 164°–166° C.

EXAMPLE 9

10,10-Dihydro-10-phenyl-10-[[(2-propenyloxy)carbonyl]imino]-10H-phenoxaphosphine A mixture of 0.5 g of hexane washed 50% sodium hydride, 50 ml of 1,2-dimethoxyethane and 0.71 ml of allyl alcohol was stirred at room temperature for 45 minutes, then 3.85 g of 10,10-dihydro-10-[(1H-imidazol-1-ylcarbonyl)imino]-10-phenyl-10H-phenoxaphosphine was added. This mixture was refluxed for 6 hours, then concentrated to dryness. Water was added to the residue, the crystals were collected and recrystallized from dichloromethanediethyl ether with charcoal treatment and refrigeration, giving 3.0 g of the desired product, mp 120°–122° C.

EXAMPLE 10

10,10-Dihydro-10-phenyl-10-[[(2-propynyloxy)-carbonyl]imino]-10H-phenoxaphosphine The procedure of Example 8 was repeated, using 0.61 ml of propargyl alcohol in place of allyl alcohol. After refluxing, the mixture was concentrated to a thick oil. This oil was partitioned between water and dichloromethane. The dichloromethane extract was taken to dryness in vacuo and the residue purified by chromatography on silica gel. Elution with 75% ethyl acetate:25% hexane, concentration of the eluate to dryness in vacuo and recrystallization from dichloromethane-diethyl ether gave 450 mg of the desired product, mp 170°–173° C.

EXAMPLE 11

10-[[(Cyclopentyloxy)carbonyl]imino]-10,10-dihydro-10-phenyl-10H-phenoxaphosphine A mixture of 0.5 g of petroleum ether washed, 50% sodium hydride, 50 ml of 1,2-dimethoxyethane and 0.63 ml of cyclopentanol was stirred for 45 minutes, then 3.85 g of 10,10-dihydro-10-[(1H-imidazol-1-ylcarbonyl)-imino]-10-phenyl-10H-phenoxaphosphine was added, the mixture was refluxed for 5 hours and then concentrated to a thick oil. Water was added, the mixture was extracted with dichloromethane and concentrated. The residue was purified by chromatography on silica gel, eluting with 75% ethyl acetate:25% hexane and recrystallized from dichloromethane-diethyl ether, giving 450 mg of the desired product, mp 170°–173° C.

EXAMPLE 12

10,10-Dihydro-10-phenyl-10-[[(3-pyridylmethoxy)-carbonyl]imino]-10H-phenoxaphosphine A 100 mg portion of 50% sodium hydride in mineral oil was added to a stirred solution of 10.9 g of 3-pyridinemethanol. After 20 minutes 17 g of 1,1'-carbonyldiimidazole was added, and stirring continued for five hours at room temperature. A 4 g portion of anhydrous hydrazine was added and the reaction mixture was stirred at room temperature for 16 hours. Remval of all volatiles in vacuo left a residue containing 3-pyridylmethylcarbazate. This was dissolved in 100 ml of water containing 25 ml of concentrated hydrochloric acid. The solution was stirred at 0°–5° C. as 8.5 g of sodium nitrate in 50 ml of water was added dropwise over 30 minutes. The solution was stirred an additional 30 minutes at 0°–5° C. and then basified to pH 8 with 10N sodium hydroxide. Extraction with 300 ml of diethyl ether and removal of the diethyl ether in vacuo left 8.7 g of 3-pyridylmethyl azidoformate. To a stirred solution of 5.5 g of 10-phenyl-10H-phenoxaphosphine in 100 ml of diethyl ether was added 4.35 g of 3-pyridylmethyl azidoformate in 25 ml of diethyl ether. Heavy gas evolution resulted immediately, and a tacky precipitate formed that crystallized abruptly on continued stirring. After one hour, the precipitate of the desired product was collected, washed with diethyl ether and dried; yield, 4.8 g; mp 135°–136° C., resolidifying and then remelting at 165°–166° C.

EXAMPLE 13

10,10-Dihydro-10-phenyl-10-[[(4-pyridylmethoxy)carbonyl]imino]-10H-phenoxaphosphine The procedure of Example 9 was repeated, using 1.2 g of 4-pyridinemethanol in place of allyl alcohol. After refluxing for 18 hours, the mixture was added to 500 ml of ice water. The precipitate was collected on a filter of diatomaceous earth. Extraction with 250 ml of boiling dichloromethane and concentration in vacuo gave a viscous oil which was dissolved in 100 ml of boiling diethyl ether. Cooling at $-10°$ C. gave 0.75 g of the desired product as white crystals, mp 137°–139° C.

EXAMPLE 14

10,10-Dihydro-10-phenyl-10-[[(2-pyridylmethoxy)-carbonyl]imino]-10H-phenoxaphosphine The procedure of Example 13 was repeated, using 1.2 g of 2-pyridinemethanol in place of 4-pyridinemethanol. The crude product was purified by chromatography on silica gel, eluting with 75% ethyl acetate:25% hexane. After removal of the solvents in vacuo, and recrystallization of the residue from diethyl ether, 183 mg of the desired product was obtained, mp 128°–129° C.

EXAMPLE 15

Preparation of Compressed Tablet

| Ingredient | mg/Tablet |
|---|---|
| 10,10-Dihydro-10-[(ethoxycarbonyl)imino]-10-phenyl-10H-phenoxaphosphine | 5–100 |
| Dibasic Calcium Phosphate NF | qs |
| Starch U.S.P. | 40 |
| Modified Starch | 10 |
| Magnesium Stearate U.S.P. | 1–5 |

EXAMPLE 16

Preparation of Hard Shell Capsule

| Ingredient | mg/Capsule |
|---|---|
| 10,10-Dihydro-10-[(ethoxycarbonyl)imino]-10-phenyl-10H-phenoxaphosphine | 5–100 |
| Lactose, Spray Dried | qs |
| Magnesium Stearate U.S.P. | 1–10 |

EXAMPLE 17

Preparation of Oral Suspension

| Ingredient | Amount |
|---|---|
| 10,10-Dihydro-10-[(ethoxycarbonyl)imino]-10-phenyl-10H-phenoxaphosphine | 1–5% |
| Veegum | 0.1–2.0% |
| Methyl paraben | 0.08% |
| Propyl paraben | 0.02% |
| Sucrose/Sorbitol | 20–80% |
| Flavor | qs |
| Water qs to | 100% |

EXAMPLE 18

10,10-Dihydro-10-imino-10-phenyl-10H-phenoxaphosphine, sulfate

To a stirred solution of 2.7 g of 10-phenyl-10H-phenoxaphosphine in 20 ml of anhydrous methanol, was added dropwise over 5 minutes, a solution of 1.1 g of hydroxylamine O-sulfonic acid in 7 ml of anhydrous methanol. The reaction mixture was stirred for 3 hours, during which time it became homogeneous, and was then filtered into 200 ml of ether and stirred for 30 minutes. The colorless solid was collected and washed with ether, giving 2.5 g of the desired product, mp 210°–218° C.

EXAMPLE 19

10-[[(1,1-Dimethylethoxy)carbonyl]imino]-10,10-dihydro-10-phenyl-10H-phenoxaphosphine To a solution of 13.8 g of 10-phenyl-10H-phenoxaphosphine in 250 ml of ether was added a solution of 11.5 g of t-butyl carbonazidate in 50 ml of ether. The mixture was stirred for 2 hours, producing vigorous gas evolution and a heavy white precipitate which was collected, washed with ether and dried in vacuo at 60° C., giving 18.0 g of the desired compound, mp 229°–231° C. (dec.).

EXAMPLE 20

10,10-Dihydro-10-imino-10-phenyl-10H-phenoxaphosphine, sulfate

A 1 g portion of 10-[[(1,1-dimethylethoxy)carbonyl]imino]-10,10-dihydro-10-phenyl-10H-phenoxaphosphine was added to 5 ml of 50% aqueous sulfuric acid. This mixture was stirred for 18 hours, then the solid was collected, washed with water, slurried in 5 ml of acetone for 30 minutes and the solid collected and dried, giving 0.2 g of the desired product, mp 215°–225° C.

EXAMPLE 21

10,10-Dihydro-10-imino-10-phenyl-10H-phenoxaphosphine, bis(trifluoroacetate)

A 1 g portion of 10-[[1,1-dimethylethoxy)-carbonyl]imino]-10,10-dihydro-10-phenyl-10H-phenoxaphosphine was added to 5 ml of trifluoroacetic acid. The solution was allowed to stand for 2 hours, then was added to 400 ml of ether and taken to dryness in vacuo. The residue was triturated with ether and the solid collected, washed with ether and dried in vacuo, giving 0.5 g of the desired product, mp 115°–118° C.

EXAMPLE 22

10,10-Dihydro-10-imino-10-phenyl-10H-phenoxaphosphine, hydrobromide

A suspension of 1.8 g of 10-[[(1,1-dimethylethoxy)-carbonyl]imino]-10,10-dihydro-10-phenyl-10H-phenoxaphosphine in 15 ml of aqueous 48% hydrobromic acid was stirred for 3 days. The insolubles were collected, washed with a little water and the triturated with 15 ml of acetone. The insoluble product was collected, washed with acetone and then dried in vacuo at 60° C., giving 0.85 g of the desired product, mp 283°–286° C.

EXAMPLE 23

10,10-Dihydro-10-imino-10-phenyl-10H-phenoxaphosphine, hydrochloride

A solution of 1.5 g of 10[[(1,1-dimethylethoxy)carbonyl]imino]-10,10-dihydro-10-phenyl-10H-phenoxaphosphine in 20 ml of dichloromethane was added to 100 ml of ethanol saturated with dry hydrogen chloride. The mixture was stirred for one day, then the solid was collected, washed with ether and dried in vacuo at 60° C., giving 0.8 g of the desired product, mp 312°–315° C.

EXAMPLE 24

10,10-Dihydro-10-imino-10-phenyl-10H-phenoxaphosphine, hydrochloride

A 1.8 g portion of 10-[[(1,1-dimethylethoxy)carbonyl]imino]-10,10-dihydro-10-phenyl-10H-phenoxaphosphine was added to 15 ml of 37% aqueous hydrochloric acid. This mixture was stirred for one hour, then the solid was collected, washed with water and acetone, and dried in vacuo, giving 0.7 g of the desired product, mp 310°–312° C.

EXAMPLE 25

10,10-Dihydro-10-[(ethoxycarbonyl)imino]-10-phenyl-10H-phenoxaphosphine

A mixture consisting of 3.9 g of 10,10-dihydro-10-imino-10-phenyl-10H-phenoxaphosphine, sulfate, 5 ml of triethylamine and 50 ml of acetonitrile is stirred as 1.2 go of ethyl chloroformate is added dropwise. The mixture is stirred for 4–8 hours and then clarified. Removal of the solvent and excess triethylamine from the filtrate gives the desired compound.

EXAMPLE 26

10,10-Dihydro-10-[(methoxycarbonyl)imino]-10-phenyl-10H-phenoxaphosphine

The procedure of Example 25 is repeated, using 1.1 g of methyl chloroformate in place of the ethyl chloroformate, giving the desired compound.

We claim:

1. The compound 10,10-dihydro-10-imino-10-phenyl-10H-phenoxaphosphine, hydrochloride.

* * * * *